United States Patent

Kaplan et al.

[11] 4,094,992
[45] June 13, 1978

[54] BENZYLIDENE DERIVATIVES

[75] Inventors: Jean-Pierre Kaplan, Plessis Robinson; Maurice Jalfre, Paris Cedex; Don Pierre Rene Lucien Giudicelli, Fontenay Sous Bois, all of France

[73] Assignee: Synthelabo, Paris, France

[21] Appl. No.: 705,938

[22] Filed: Jul. 16, 1976

[30] Foreign Application Priority Data

Aug. 1, 1975  France ........................ 75 24065

[51] Int. Cl.² .......................................... C07C 103/29
[52] U.S. Cl. .................................. 424/324; 260/519; 260/404; 260/559 D; 260/559 A; 260/559 P; 260/591; 260/559 R; 424/309; 424/319; 560/35
[58] Field of Search ............ 260/559 A, 519, 559 D, 260/562 N, 559 D, 559 B, 566 R; 424/324

[56] References Cited

U.S. PATENT DOCUMENTS

| 3,371,085 | 2/1968 | Reeder | 260/562 N |
| 3,429,874 | 2/1969 | Topliss | 260/562 N |

OTHER PUBLICATIONS

Halpern et al., Aust. J. Chem. 1974, vol. 27, pp. 2047–2051.
Al-Sayyab et al., J. Chem. Soc. (c) 1968, pp. 406–410.

*Primary Examiner*—Arthur P. Demers

*Attorney, Agent, or Firm*—Stevens, Davis, Miller & Mosher

[57] ABSTRACT

Compounds of the formula:

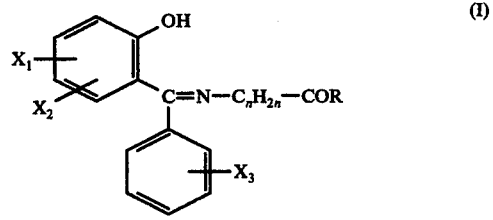

(I)

in which $X_1$, $X_2$ and $X_3$, which are identical or different each represent hydrogen, halogen, methyl, or methoxy, $n$ represents an integer from 1 to 10, and R represents hydroxyl, OM, $NH_2$, $NH(CH_2)_3$—COH, —$NH(CH_2)_3$—COOM, (where M represents an alkali metal atom), $NH(CH_2)_3$—$COOC_2H_5$, NH-cycloalkyl, NH-phenyl, NH-benzyl (where the benzyl radical is unsubstituted or substituted by halogen or trifluoromethyl), NH-alkyl, N(alkyl)₂ and N-(alkyl)-(benzyl), the aforesaid alkyls being straight or branched and having from 1 to 4 carbon atoms and the aforesaid cycloalkyls having from 3 to 6 carbon atoms, except that when $X_1$ and $X_3$ are both hydrogen, $n$ is 1 and R is OH, $X_2$ is not chlorine in the 5-position are useful in the treatment of epilepsy by oral or parenteral administration.

13 Claims, No Drawings

BENZYLIDENE DERIVATIVES

γ-Aminobutyric acid (GABA) is considered to act on the central nervous system as an inhibitor of neurotransmission. (See "GABA in nervous system transmission", Roberts E., Chase T. N., and Tower D. B. Raven Press 1976). Some authors (ibid., and "Epilepsy and γ-aminobutyric acid-mediated inhibition", Meldrum B. S., Int. Rev. Neurobiol, 12, Academic Press 1975) have shown that compounds capable of increasing the cerebral concentration of GABA by blocking its enzymatic degradation possess antiepileptic activity. GABA itself has been used with success in some cases of epilepsy (Roberts et al, loc. cit. pages 461–478). However the fact that very large quantities of GABA need to be administered to obtain the desired therapeutic effect and the fact that GABA does not easily cross the blood-brain barrier and does not therefore penetrate the central nervous system after oral or parenteral administration (Van Gelder N. M., J. of Neurochem., 12, pp 239–244, 1965), suggest that an antiepileptic effect following the administration of GABA is connected with a mechanism in which GABA does not act as an inhibitor of central nervous transmission. Further, the administration of GABA leads to substantial sideeffects (hypotension, bradycardia, and sedation).

The applicants have synthesised a family of new products which can be considered as possessing a "GABA-mimetic" activity; these compounds are capable of penetrating directly into the brain, providing it with the defence mechanism necessary to prevent or cure epileptic crises, when they are administered by the usual routes (oral, endo-rectal or parenteral).

The present invention thus provides the α-phenylbenzylidene derivatives of the general formula:

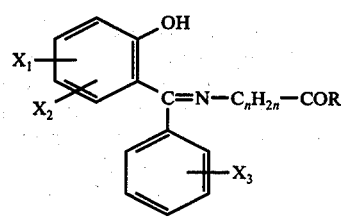

in which $X_1$, $X_2$ and $X_3$, which are identical or different, each represent, independently of one another, a hydrogen or halogen atom, especially chlorine or fluorine, or a methyl or methoxy radical, $n$ represents an integer from 1 to 10, and R represents hydroxyl, OM, $NH_2$, $NH(CH_2)_3$—COOH, —$NH(CH_2)_3$—COOM, (where M represents an alkali metal atom, in particular sodium), $NH(CH_2)_3$—$COOC_2H_5$, NH-cycloalkyl, NH-phenyl, NH-benzyl (where the benzyl radical is unsubstituted or substituted by halogen or/and trifluoromethyl), NH-alkyl, N-(alkyl)$_2$ and N-(alkyl)(benzyl), the aforesaid alkyls being straight or branched and having from 1 to 4 carbon atoms and the aforesaid cycloalkyls having from 3 to 6 carbon atoms, except that when $X_1$ and $X_3$ are both hydrogen $n$ is 1 and R is OH, $X_2$ is not chlorine in the 5-position.

The compounds of the invention can be used in human and veterinary therapy, especially as antiepileptic agents, because of their activity on the cerebral metabolism.

They can be prepared by application of known methods, and in particular by the following reaction:

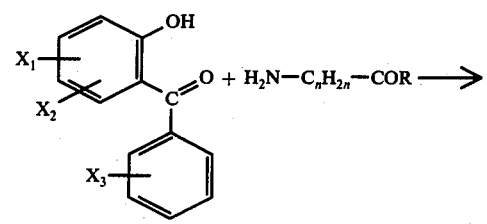

wherein the symbols have the same meaning as in the formula (I).

This reaction is advantageously carried out in a polar solvent, such as an alcohol or a glycol, in particular methanol or ethanol which can contain a little water, at a temperature between 10° C and the boiling point of the solvent, and in the presence of an alkali metal, an alkali metal alcoholate or an alkali metal hydroxide or a quaternary hydroxy-ammonium hydroxide such as Triton B.

The amides can also be prepared from the corresponding acid by reaction between the acid

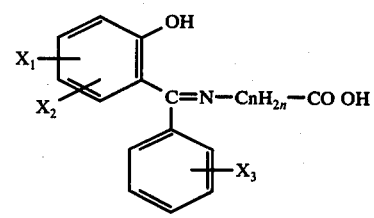

and the corresponding amine RH in the presence of carbonyl-diimidazole:

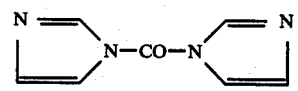

The benzophenone starting materials may be prepared from the corresponding benzoic acids in accordance with the following scheme:

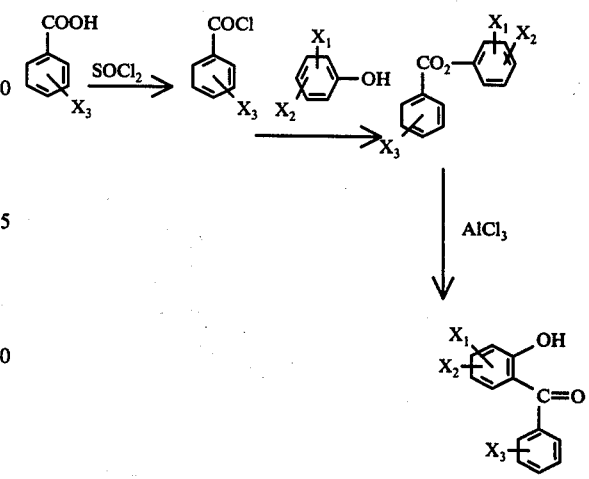

The non-limiting Examples which follow illustrate how the invention may be carried out. Temperatures are in degrees C.

EXAMPLE 1

Sodium 4-N-(α-phenyl-5-fluoro-2-hydroxy-benzylidenyl-)amino-butyrate

[(I); $X_1 = 5-F$, $X_2 = X_3 = H$, $n = 3$, $R = ONa$; code number : SL-D.0.10]

5 g of 4-aminobutyric acid and 11.5 g of 2-hydroxy-5-fluoro-benzophenone are dissolved in 500 ml of ethanol and 10 ml of 5.3 N sodium methylate are added. A limpid solution is obtained, which is evaporated under reduced pressure. The residue is dissolved in water and 4-N-(α-phenyl-5-fluoro-2-hydroxy-benzylidenyl)-amino-butyric acid is precipitated, in the form of an oil, by adding 0.1 N citric acid until the pH is 4. This acid is purified by dissolving it in alcohol, evaporating the solution and crystallising the residue from petroleum ether. 10.2 g of the acid (yield = 70%) are collected. The acid melts at 101°.

This acid is converted to its sodium salt in the following manner. 10.3 ml of a 3.14 N sodium methylate solution are added to 9.8 g of acid dissolved in 500 ml of absolute ethanol. The solution obtained is evaporated to dryness and the residue is filtered on a glass frit, onto which it is washed with ether. It is suction-drained, and dried in a vacuum desiccator. 10.3 g (yield = 98%) of sodium 4-N-(α-phenyl-5-fluoro-2-hydroxy-benzylidenyl)amino-butyrate, decomposing substantially at 250°, are thus obtained.

Analysis: Calculated %: C 63.16: H 4.68: N 4.33: Na 7.11: Found %: C 63.09: H 4.67: N 4.28: Na 7.14: C 63.06: H 4.65: N 4.33: Na -.

The IR and NMR spectra have confirmed the structure of the compound.

EXAMPLE 2

Sodium 4-N-[α-(3-fluorophenyl)-5-fluoro-2-hydroxybenzylidenyl]-amino-butyrate

[(I); $X_1 = 5-F$, $X_2 = H$, $X_3 = 3-F$, $R = ONa$, $n = 3$; code number: Sl-D.044].

The following are obtained successively by a method entirely similar to that described in Example 1:

4-N-[α-(3-Fluorophenyl)-5-fluoro-2-hydroxybenzylidenyl]-amino-butyric acid, in a yield of 42.2%, melting point = 84.5°–85.5°, and the corresponding sodium salt, in a yield of 85.3%; melting point = 202° (decomposition).

Analysis: Cac. % (with 1.08% of water): C 59.18: H 4.21: N 4.06: F 11.00: Na 6.67: Found %: C 59.26: H 4.32: N 3.96: F 10.67: Na 6.80: C 59.24: H 4.32: N 3.91: F 10.75: Na -.

The IR and NMR spectra have confirmed the structure of the compound.

EXAMPLE 3

Sodium 4-N-[α-(4-fluorophenyl)-5-fluoro-2-hydroxybenzylidenyl]-amino-butyrate

[(I); $X_1 = 5-F$, $X_2 = H$, $X_3 = 4-F$, $n = 3$, $R = ONa$; code number: SL-D.045]

5.2 g (0.0505 mol) of 4-aminobutyric acid, 2.0 g (0.0505 mol) of powdered sodium hydroxide and 12 g (0.0512 mol) of 5,4'-difluoro-2-hydroxy-benzophenone are introduced into a 500 ml flask. 300 ml of ethanol and a few drops of water are added in order to dissolve the whole batch. The mixture is then evaporated under reduced pressure at 30°. An orange-yellow solid is obtained, which is dissolved in two liters of water, and the solution is acidified to pH 4 with citric acid. The pasty precipitate obtained is taken up in four liters of ether. The ether solution is dried and concentrated. An orange oil is thus obtained, which crystallises on trituration which petroleum ether. Recrystallisation from cyclohexane gives 4-N-[α-(4-fluorophenyl)-5-fluoro2-hydroxy-benzylidenyl]-amino-butyric acid, melting point = 89.5°–90°, in a yield of 52.5%.

The sodium salt of this acid is prepared in accordance with the method described in Example 1. It is obtained in a yield of 85.7%. It melts at 231° (with decomposition).

Analysis: Calc. % (with 2.05% of water): C 58.60: H 4.28: N 4.02: F 10.90: Na 6.60: Found %: C 59.07: H 4.33: N 3.93: F 10.69: Na -: C 58.97: H 4.27: N 3.93: F 10.87: Na 6.28.

The IR and NMR spectra have confirmed the structure of this compound.

EXAMPLE 4

2-N-[α-(3-Chlorophenyl)-5-fluoro-2-hydroxybenzylidenyl]-amino-acetamide

[(I); $X_1 = 5-F$, $X_2 = H$, $X_3 = 3-Cl$, $n = 1$, $R = NH_2$; code number: SL-D.039]

6.73 ml of 3.14 N sodium methylate (0.021 mol) and 200 ml of methanol are added to a stirred suspension of 2.34 g (0.021 mol) of glycinamide in 200 ml of methanol. The mixture is stirred for 10 minutes and about 5 ml of water are added, after which stirring is continued until solution is complete. 5.5 g (0.022 mol) of 3'-chloro-5-fluoro-2-hydroxy-benzophenone are then introduced and the mixture is evaporated to dryness under reduced pressure.

The residue is taken up in 200 ml of ether and 200 ml of methanol and is again evaporated under reduced pressure. This operation is repeated several times. Finally, the 2-N-[α-(3-chlorophenyl)-5-fluoro2-hydroxybenzylidenyl]-amino-acetamide is crystallised by trituration with petroleum ether. 4.1 g of the product are collected, representing a yield of 63.2%. The compound melts at 160°.

Analysis: Calc. % (with 0.22% of water): C 58.61: H 3.95: N 9.11: Found %: C 58.47: H 4.15: N 9.09: C 58.44: H 4.05: N -.

The IR and NMR spectra have confirmed the structure of the compound.

EXAMPLE 5

Sodium 11-N-(α-phenyl-2-hydroxy-benzylidenyl)amino-undecanoate

[(I); $X_1 = X_2 = X_3 = H$; $n = 10$; $R = ONa$; code number: SL-D.075]

Using the method described in Example 1, the following are obtained successively: 11-N-(α-phenyl-2-hydroxy-benzylidenyl)-amino-undecanoic acid, melting point = 74.5°–75.5°, and its sodium salt, melting point 236°–240° (decomposition).

Analysis: Calculated %: C 71.44: H 7.49: N 3.47: Na 5.70: Found %: C 71.75: H 7.37: N 3.29: Na 5.65: C 71.57: H 7.55: N 3.48: Na -.

The IR and NMR spectra have confirmed the structure of the compound.

EXAMPLE 6

4-[α(4-Chlorophenyl)-5-fluoro-2-hydroxy-benzylidenyl]-amino-butyramide ($X_1 = 5-F$; $X_2 = H$; $X_3 = 4-Cl$; n = 3; R = $NH_2$; code number: SLE 002)

22.3 g (0.1375 mol) of 95% pure carbonyldiimidazole are added in portions, over the course of 10 minutes, to a solution, stirred at 0°, of 42 g (0.125 mol) of 4-[α-(4-chlorophenyl)-5-fluoro-2-hydroxy-benzylidenyl]-amino-butyric acid in 130 ml of anhydrous THF, and the mixture is stirred in the cold for 15 minutes and then at ambient temperature for 15 minutes. The solution obtained is added dropwise, whilst stirring, to 800 ml of liquid ammonia and the mixture is stirred until evaporation is complete.

The oily residue is taken up in 500 ml of chloroform and the solution is washed with water, an aqueous bicarbonate solution and again with water. It is dried over $MgSO_4$ in the presence of vegetable charcoal and filtered, and the filtrate is evaporated to dryness. An oil is obtained, which crystallises by trituration in petroleum ether. The product is washed onto a frit with petroleum ether, and is there washed with petroleum ether and suction-drained to the maximum extent. It is recrystallised from a 1:1 mixture of cyclohexane and toluene, with treatment with vegetable charcoal, and is dried in a heated vacuum desiccator at 60°.

Weight obtained: 28 g; yield: 67%; melting point = 133°–135° (Tottoli).

Analysis Calculated %: C 60.99: H 4.82: N 8.37: Cl 10.59: F 5.67: Found %: C 60.91: H 4.83: N 8.36: Cl 10.84: F 5.74: C 60.97: H 4.78: N 8.26: Cl 10.73: F 5.76.

Table I provides the formulae and characteristics of a certain number of other compounds of the general formula (I) prepared according to Examples 1 to 6 or of minor variants of the methods described therein. The analyses and spectra in all cases confirmed the structure of the products obtained.

TABLE I

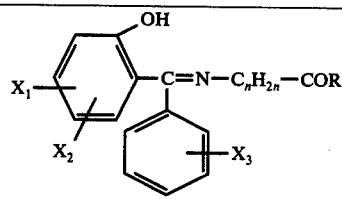

Examples 7 to 58

| Code number | $X_1$ | $X_2$ | $X_3$ | n | R | Characteristics |
|---|---|---|---|---|---|---|
| SL-C.227 | H | H | H | 3 | ONa | melting point = 218° |
| SL-D.005 | 5-Cl | H | H | 3 | ONa | melting point of the acid = 128°; melting point = 239–42° (decomposition) |
| SL-D.006 | H | H | H | 4 | ONa | melting point of the acid = 133–4°; melting point = 206° |
| SL-D.007 | H | H | H | 1 | ONa | melting point of the acid = 170–171°; melting point > 260° |
| SL-D.016 | 5-F | H | 3-Cl | 3 | ONa | melting point of the acid = 170°; melting point > 260° |
| SL-D.017 | 5-F | H | 2F | 3 | ONa | melting point of the acid = 100°; melting point > 280° |
| SL-D.019 | H | H | H | 2 | ONa | melting point of the acid = 90°; melting point = 240° (decomposition) |
| SL-D.026 | 5-$CH_3$ | H | H | 3 | ONa | melting point of the acid = 185–6°; melting point = 239–240° |
| SL-D.027 | 5-F | H | 2-Cl | 3 | ONa | melting point of the acid = 120°; melting point = 228–230° |
| SL-D.029 | 5-F | H | 2-$CH_3$ | 3 | ONa | the acid is an oil; melting point > 260° (decomposition) |
| SL-D.037 | H | H | H | 1 | $NH_2$ | melting point = 140° |
| SL-D.038 | 5-Cl | H | 2F | 3 | ONa | melting point = 230° (decomposition) |
| SL-D.046 | H | H | 2-F | 3 | ONa | melting point of the acid = 96°; melting point = 178–9° |
| SL-D.053 | 5-$CH_3$ | H | 2-F | 3 | ONa | melting point of the acid = 96.5–97.5°; melting point > 260° (decomposition) |
| SL-D.054 | 5-F | H | H | 10 | ONa | melting point = 230° (decomposition) |
| SL-D.055 | 5-F | H | 3-F | 1 | $NH_2$ | melting point of the acid = 79°; melting point = 129.5–131° |
| SL-D.059 | 5-F | H | H | 5 | ONa | melting point = 236° (decomposition) |
| SL-D.074 | H | H | H | 5 | ONa | melting point of the acid = 129–130°; melting point = 210–12° (decomposition) |
| SL-D.078 | H | H | 2-Cl | 3 | ONa | melting point of the acid 32 123–4°; melting point = 230°–5° |
| SL-D.083 | 5-F | H | H | 1 | $NH_2$ | melting point of the acid = 93–94°; melting point = 127–128° |
| SL-D.100 | H | H | H | 7 | ONa | melting point = 221–4° (decomposition) |
| SL-D.102 | 5-F | H | 4-Cl | 3 | ONa | melting point of the acid = 92–93°; melting point = 231–6° (decomposition) |
| SL-D.106 | 5-F | H | H | 4 | ONa | melting point of the acid = 91.5–93°; melting point = 300° (decomposition) |
| SL-D.107 | 4-$OCH_3$ | H | H | 3 | ONa | melting point of the acid = 178°; melting point = 200–200.5° |
| SL-D.118 | 4-$OCH_3$ | H | 4-Cl | 3 | ONa | melting point of the acid = 134.5–135°; melting point = 175–180° (decomposition) |
| SL-D.136 | 5-$CH_3$ | H | 2-Cl | 3 | ONa | melting point of the acid = 122–123°; melting point = 244–245° (decomposition) |
| SL-D.138 | 4-$CH_3$ | 5-Cl | H | 3 | ONa | melting point of the acid = 85–87°; melting point = 240–245° (decomposition) |
| SL-D.166 | 5-F | H | 4-F | 3 | $NH_2$ | melting point of the acid = 123.5–124°; melting point = 146.5–148° |
| SL-D.167 | 5-F | H | H | 3 | $NH_2$ | melting point = 144° |

TABLE I-continued

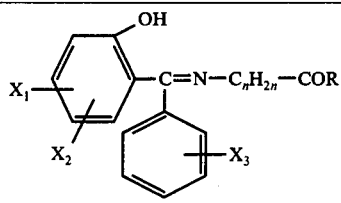

Examples 7 to 58

| Code number | $X_1$ | $X_2$ | $X_3$ | n | R | Characteristics |
|---|---|---|---|---|---|---|
| SL-D.168 | 5-F | H | H | 3 | —NH(CH$_2$)$_3$—COO—C$_2$H$_5$ | melting point = 92° |
| SL-D.179 | 5-F | H | 4-F | 3 | —NH(CH$_2$)$_3$—COO—C$_2$H$_5$ | melting point = 107–108° |
| SL-D.207 | 5-F | H | 4-F | 3 | —NH(CH$_2$)$_3$—COONa | melting point = 109–116°<br>melting point of the acid = 99–100.5° |
| SL-D146 | 4-Br | H | H | 3 | —ONa | melting point = 220–227° (decomposition)<br>melting point of the acid 119–120.5° |
| SL-D.157 | 4-Cl | H | H | 3 | —ONa | melting point = 224–232° (decompositon)<br>melting point of the acid = 115.5–116.5° |
| SL-D.156 | 5-F | H | 3-CH$_3$ | 3 | —ONa | melting point >260° (decomposition)<br>melting point of the acid = 107.5–108.5° |
| SLE-002 | 5 F | H | 4 Cl | 3 | —NH$_2$ | melting point = 133–135° |
| SLE-009 | 5 F | H | H | 3 | —NH—C$_6$H$_{11}$ (cyclohexyl) | melting point — 154° |
| SLE-010 | 5 F | H | H | 3 | —NH—cyclopropyl | melting point = 127° |
| SLE-011 | 5 F | H | H | 3 | —NH—cyclopentyl | melting point = 124° |
| SLE-012 | 5 F | H | H | 3 | —NH—phenyl | melting point = 178° |
| SLE-013 | 5 F | H | H | 3 | —NH—CH$_2$—phenyl | melting point = 99° |
| SLE-015 | 5F | H | H | 3 | —N(H)(CH$_3$) | melting point = 114° |
| SLE-022 | 5 F | H | H | 3 | —N(CH$_3$)$_2$ | melting point = 118° |
| SLE-023 | 5 F | H | H | 3 | —N(n-C$_4$H$_9$)$_2$ | melting point = 55–56° |
| SLE-030 | 5 F | H | H | 3 | —NH—cyclobutyl | melting point = 117° |
| SLE-031 | 5 F | H | H | 3 | —NH—CH(CH$_3$)$_2$ | melting point = 136° |
| SLE-085 | 5 F | H | H | 6<br>$C_nH_{2n}$ = CH$_2$—CH$_2$—CH(CH$_3$CH$_2$CH$_2$) | | ONa | acid = 85–86°<br>melting point = 237–240° decomposition |
| SLE-086 | 5 F | H | 2 Cl | 3 | NH$_2$ | melting point = 110–111.5° |
| SLE-091 | 5 F | H | 3 Cl | 3 | —NH$_2$ | melting point = 118–119° |
| SLE-117 | 5 F | H | H | 3 | —NH—CH$_2$—(4-F-phenyl) | melting point = 106–107° |

TABLE I-continued

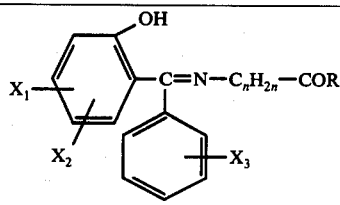

Examples 7 to 58

| Code number | $X_1$ | $X_2$ | $X_3$ | n | R | Characteristics |
|---|---|---|---|---|---|---|
| SLE 118 | 5 F | H | H | 3 | $-N<\genfrac{}{}{0pt}{}{CH_3}{CH_2-C_6H_5}$ | liquid |
| SLE 134 | 5 F | H | H | 3 | $-NH-CH_2-C_6H_4-CF_3$ | melting point = 113.5–114.5° |

The compounds of the invention have been subjected to a series of pharmacological tests which have revealed their valuable properties.

I. Acute toxicity in mice

The compounds of the invention and the reference substances were administered intraperitoneally to $CD_1$ mice. The 50% lethal dose (LD 50) was determined graphically. The number of dead animals 48 hours after intraperitoneal administration was recorded. The results are summarised in Table II.

II. GABA-mimetic activity of the compounds (I)

This activity is demonstrated by the antagonism to convulsions induced by bicuculline in mice. The experimental method of Curtis, D. R., et al., Brain Res., 1971, 33, 57 and Perez de la Mora, N., Biochem. Pharmacol., 1973, 22, 2,635, was used.

Bicuculline is a relatively selective blocking agent for GABA-sensitive post-synaptic receptors and its convulsive and lethal effects are antagonised by compounds which raise the cerebral concentration of GABA or possess a GABA-mimetic activity. The 50% active doses (AD 50), namely the doses which protect 50% of the animals against the effect of bicuculline, were evaluated for the substances studied. The results are presented in Table II.

TABLE II

| PRODUCTS | LD 50 (intraperitoneal administration in mice, mg/kg) | Anti-bicuculline activity, AD 50 (intraperitoneal administration), mg/kg |
|---|---|---|
| SL 74,227 | 975 | 500 |
| 75,005 | 350 | 120 |
| 75,006 | 700 | 250 |
| 75,010 | 600 | 125 |
| 75,017 | 525 | 175 |
| 75,019 | 850 | 425 |
| 75,027 | 375 | 125 |
| 75,029 | 475 | 250 |
| 75,037 | 1,350 | 200 |
| 75,038 | 345 | 115 |
| 75,044 | 850 | 250 |
| 75,045 | 650 | 125 |
| 75,046 | 675 | 225 |
| 75,050 | 860 | 300 |
| 75,053 | 600 | 125 |
| 75,054 | 300 | 130 |
| 75,059 | 800 | 200 |
| 75,074 | 750 | 300 |
| 75,075 | 210 | 100 |
| 75,078 | 350 | 110 |
| 75,083 | 650 | 175 |
| 75,100 | 600 | 300 |
| 75,102 | 500 | 65 |
| SL 75,106 | 600 | 120 |
| 75,107 | 950 | 450 |
| 75,118 | 525 | 225 |
| 75,136 | 350 | 110 |
| 75,166 | >2,000 | 180 |
| 75,167 | >2,000 | 100 |
| 75,168 | 975 | 500 |
| 76,002 | 900 | 65 |
| 76,010 | 1,250 | 250 |
| 76,011 | >2,000 | 365 |
| 76,012 | >2,000 | 500 |
| 76,013 | >2,000 | 200 |
| 76,022 | 1,400 | 350 |
| 76,023 | 1,700 | 300 |
| 76,030 | >2,000 | 200 |
| 76,031 | >2,000 | 500 |
| 76,085 | 235 | 50 |
| 76,091 | 600 | 300 |
| GABA | >4,000 | >4,000 |
| CETYL-GABA | 470 | 60 |
| PIRACETAM | >4,000 | 500 |

The compounds of the invention, which are very active as anti-convulsants and of low toxicity, are therefore of great therapeutic interest in human and veterinary medicine in different types of epilepsy.

The invention consequently comprises pharmaceutical compositions which contain the compounds of formula (I) as active principles, in association with any compatible pharmaceutically acceptable excipients suitable for their administration, in particular their oral or parenteral administration. These pharmaceutical compositions can also contain other medicaments with which the compounds (I) are pharmacologically and therapeutically compatible.

For oral administration, any of the usual forms appropriate for this method of administration may be used, such as tablets, dragees, pills, capsules, cachets and potable solutions or suspensions, the unit weight of active principle being able to vary between 1 and 40 mg, and the daily posology between 5 and 400 mg.

For parenteral administration, sterile solutions prepared beforehand or at the time of use, and buffered to the physiological pH, are used. These solutions contain 0.5 to 10 mg of active principle in a volume of 1 to 5 ml. In practice, they are divided into ampoules containing from 1 to 5 ml, for administration by intramuscular or intravenous injection, or for administration by slow intravenous infusion. The daily dose for parenteral administration can be between 2 and 100 mg.

We claim:

1. Compound of claim 1

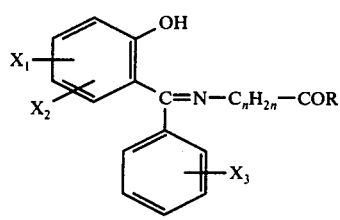

in which one of $X_1$ and $X_3$ is halogen, methyl, or methoxy, and $X_2$ and the other of $X_1$ and $X_3$ are each independently hydrogen, halogen, methyl or methoxy, $n$ represents an integer from 1 to 10, and R is $NH_2$, $NH$-($C_{3-6}$ cycloalkyl), NH-phenyl, NH-benzyl, NH-($C_{1-4}$ alkyl), N-($C_{1-4}$ alkyl)$_2$ or N-($C_{1-4}$ alkyl)-(benzyl), where each benzyl may be substituted by halogen and/or trifluoromethyl.

2. A compound according to claim 1 in which one or more of $X_1$, $X_2$ and $X_3$ is chlorine or bromine.

3. A compound according to claim 1, in which R is $NH_2$.

4. A compound

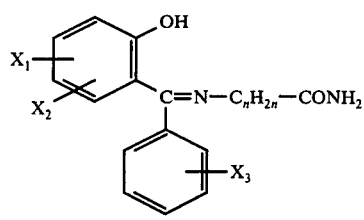

wherein each of $X_1$, $X_2$ and $X_3$ is independently selected from hydrogen, chlorine, fluorine, methyl or methoxy and $n$ is an integer of 1 to 10.

5. A compound according to claim 4, in which $X_1$ is a substituent in the 4- or 5-position and $X_2$ is a hydrogen atom.

6. A compound according to claim 5 which is 4-N-[α-(4-chlorophenyl)-5-fluoro-2-hydroxy-benzylidenyl]-amino-butyramide.

7. Compound of claim 1 of the formula:

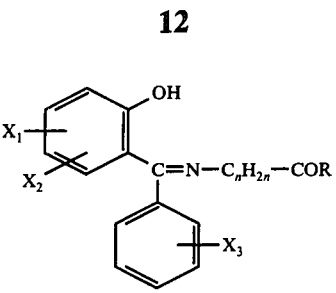

in which one of $X_1$ and $X_3$ is halogen, methyl, or methoxy, and $X_2$ and the other of $X_1$ and $X_3$ are each independently hydrogen, halogen, methyl or methoxy, $n$ represents an integer from 1 to 10, and R represents $NH_2$, $NH$—($C_{1-4}$ alkyl), or $N(C_{1-4}$ alkyl)$_2$.

8. Compound of claim 1 of the formula:

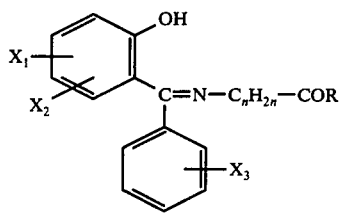

in which one of $X_1$ and $X_3$ is halogen, methyl, or methoxy, and $X_2$ and the other of $X_1$ and $X_3$ are each independently hydrogen, halogen, methyl or methoxy, $n$ represents an integer from 1 to 10, and R represents $NH$-($C_{3-6}$ cycloalkyl).

9. Compound of claim 1 of the formula:

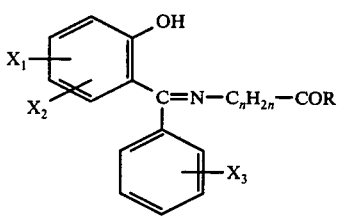

in which one of $X_1$ and $X_3$ is halogen, methyl, or methoxy, and $X_2$ and the other of $X_1$ and $X_3$ are each independently hydrogen, halogen, methyl or methoxy, $n$ represents an integer from 1 to 10, and R represents NH-phenyl, NH-benzyl, or N-($C_{1-4}$ alkyl)-(benzyl) where the benzyl radical is unsubstituted or substituted by halogen or trifluoromethyl.

10. A compound according to claim 5 which is 4-N-[α-phenyl-5-fluoro-2-hydroxy-benzylidenyl]-amino-butyramide.

11. A compound according to claim 5 which is N-(4-fluorobenzyl)-4-N-[α-phenyl-5-fluoro-2-hydroxy-benzylidenyl]-amino-butyramide.

12. A pharmaceutical composition suitable for the treatment of epilepsy comprising, as an active ingredient, an amount of a compound of claim 1 effective for treating epilepsy in association with a significant amount of a compatible pharmaceutically acceptable excipient.

13. A method of treating epilepsy which comprises administering to a subject liable to epilepsy an effective amount of a compound of claim 1 sufficient to relieve said epilepsy.

* * * * *

UNITED STATES PATENT AND TRADEMARK OFFICE
CERTIFICATE OF CORRECTION

PATENT NO. : 4,094,992
DATED : June 13, 1978
INVENTOR(S) : Jean-Pierre KAPLAN et al.

It is certified that error appears in the above-identified patent and that said Letters Patent is hereby corrected as shown below:

Claim 1, line 1, change "Compound of claim 1" to --Compound of formula--.

Signed and Sealed this

Fourth Day of December 1984

[SEAL]

Attest:

GERALD J. MOSSINGHOFF

*Attesting Officer*     *Commissioner of Patents and Trademarks*